United States Patent
Yilmaz

(10) Patent No.: US 12,280,205 B2
(45) Date of Patent: Apr. 22, 2025

(54) AEROSOL PROVISION DEVICE FOR GENERATING A FLOW OF AEROSOL

(71) Applicant: Nicoventures Trading Limited, London (GB)

(72) Inventor: Ugurhan Yilmaz, London (GB)

(73) Assignee: NICOVENTURES TRADING LIMITED, London (GB)

( * ) Notice: Subject to any disclaimer, the term of this patent is extended or adjusted under 35 U.S.C. 154(b) by 144 days.

(21) Appl. No.: 17/882,085

(22) Filed: Aug. 5, 2022

(65) Prior Publication Data

US 2022/0369710 A1 Nov. 24, 2022

Related U.S. Application Data

(63) Continuation of application No. 16/758,977, filed as application No. PCT/EP2018/079139 on Oct. 24, 2018, now Pat. No. 11,439,778.

(30) Foreign Application Priority Data

Oct. 24, 2017 (GB) ...................................... 1717498

(51) Int. Cl.
*A24F 40/30* (2020.01)
*A24F 40/42* (2020.01)
(Continued)

(52) U.S. Cl.
CPC .............. *A61M 15/06* (2013.01); *A24F 40/30* (2020.01); *A24F 40/42* (2020.01); *A24F 40/44* (2020.01);
(Continued)

(58) Field of Classification Search
CPC .......... A24F 40/10; A24F 40/20; A24F 40/30; A24F 40/42; A24F 40/44; A24F 40/46;
(Continued)

(56) References Cited

U.S. PATENT DOCUMENTS 4,790,332 A * 12/1988 Wallace .................. A24F 13/18
131/330
4,911,181 A 3/1990 Vromen et al.
(Continued)

FOREIGN PATENT DOCUMENTS

CA 3010559 A1 7/2017
CL 2017003355 A1 6/2018
(Continued)

OTHER PUBLICATIONS

Notice of Reasons for Rejection received for Japanese Patent Application No. 2021-068570, mailed on Dec. 20, 2022, 9 pages (4 pages of English Translation and 5 pages of Official Copy).
(Continued)

*Primary Examiner* — Abdullah A Riyami
*Assistant Examiner* — Thang H Nguyen
(74) *Attorney, Agent, or Firm* — Husch Blackwell

(57) ABSTRACT

An aerosol provision device includes a first section for containing an aerosolizable substance from which a flow of aerosol can be generated; and a second section for containing a material. In use, a flow of aerosol generated from aerosolizable substance in the first section flows through material in the second section before being inhaled by a user. The first section and the second section are located in a side-by-side arrangement in the device.

28 Claims, 5 Drawing Sheets

(51) Int. Cl.
*A24F 40/44* (2020.01)
*A24F 40/46* (2020.01)
*A24F 40/485* (2020.01)
*A61M 15/06* (2006.01)
*A24F 40/10* (2020.01)
*A24F 40/20* (2020.01)

(52) U.S. Cl.
CPC ............ *A24F 40/46* (2020.01); *A24F 40/485* (2020.01); *A24F 40/10* (2020.01); *A24F 40/20* (2020.01)

(58) Field of Classification Search
CPC ............... A24F 40/485; A61M 11/042; A61M 15/0003; A61M 15/0023; A61M 15/06; A61M 2016/0024; A61M 2205/8206
See application file for complete search history.

(56) References Cited

U.S. PATENT DOCUMENTS

| | | | |
|---|---|---|---|
| 5,135,009 | A | 8/1992 | Muller et al. |
| 5,880,439 | A * | 3/1999 | Deevi .................... H01C 17/30 219/535 |
| 7,278,283 | B2 | 10/2007 | Meckbach |
| 9,004,073 | B2 | 4/2015 | Tucker et al. |
| 9,101,729 | B2 | 8/2015 | Liu |
| 9,462,830 | B2 * | 10/2016 | Liu .......................... A24F 40/30 |
| 10,375,996 | B2 * | 8/2019 | Aoun ..................... A61M 11/042 |
| 10,842,189 | B1 * | 11/2020 | Hermiz ................... G05B 15/02 |
| 11,129,413 | B2 * | 9/2021 | Lipowicz ................ A24F 40/42 |
| 11,229,413 | B2 * | 1/2022 | Davidson ................ A61M 15/06 |
| 11,259,758 | B2 * | 3/2022 | Modai ..................... A61B 5/6898 |
| 2007/0102013 | A1 | 5/2007 | Adams et al. |
| 2008/0276948 | A1 | 11/2008 | Gedevanishvili et al. |
| 2013/0014772 | A1 | 1/2013 | Liu |
| 2013/0074857 | A1 | 3/2013 | Buchberger |
| 2013/0319407 | A1 | 12/2013 | Liu |
| 2013/0333700 | A1 | 12/2013 | Buchberger |
| 2014/0000638 | A1 | 1/2014 | Sebastian et al. |
| 2014/0041655 | A1 | 2/2014 | Barron et al. |
| 2014/0166029 | A1 | 6/2014 | Weigensberg et al. |
| 2014/0314397 | A1 | 10/2014 | Alima |
| 2015/0374039 | A1 | 12/2015 | Zhu |
| 2016/0015081 | A1 | 1/2016 | Liu |
| 2016/0106153 | A1 | 4/2016 | Zhu |
| 2016/0135505 | A1 | 5/2016 | Li et al. |
| 2016/0135506 | A1 | 5/2016 | Sanchez et al. |
| 2016/0178377 | A1 | 6/2016 | Jung et al. |
| 2016/0192713 | A1 | 7/2016 | Memari et al. |
| 2016/0262449 | A1 | 9/2016 | Liu |
| 2016/0262452 | A1 | 9/2016 | Zhu |
| 2016/0270438 | A1 | 9/2016 | Jackson et al. |
| 2016/0295919 | A1 | 10/2016 | Thomas, Jr. |
| 2016/0324216 | A1 | 11/2016 | Li et al. |
| 2016/0345626 | A1 | 12/2016 | Wong et al. |
| 2016/0366941 | A1 | 12/2016 | Lin |
| 2017/0035117 | A1 | 2/2017 | Lin |
| 2017/0042252 | A1 | 2/2017 | Takeuchi et al. |
| 2017/0238606 | A1 | 8/2017 | Matsumoto et al. |
| 2017/0238614 | A1 | 8/2017 | Li et al. |
| 2019/0001087 | A1 * | 1/2019 | Davidson ............ A61M 11/041 |
| 2019/0053544 | A1 | 2/2019 | Yamada et al. |
| 2019/0142069 | A1 * | 5/2019 | Qiu ....................... A24F 40/485 131/329 |
| 2020/0324066 | A1 | 10/2020 | Potter |
| 2020/0350736 | A1 | 11/2020 | Jung et al. |
| 2020/0383379 | A1 * | 12/2020 | Yilmaz .................. A24F 40/46 |
| 2021/0030981 | A1 | 2/2021 | Azzopardi et al. |
| 2021/0329976 | A1 * | 10/2021 | Nelson ................... A24F 40/42 |

FOREIGN PATENT DOCUMENTS

| | | |
|---|---|---|
| CL | 2018002292 A1 | 12/2018 |
| CL | 2018003164 A1 | 2/2019 |
| CL | 2018003426 A1 | 3/2019 |
| CL | 2019001317 A1 | 8/2019 |
| CL | 2019001161 A1 | 9/2019 |
| CL | 2019002751 A1 | 2/2020 |
| CN | 201294864 Y | 8/2009 |
| CN | 201591126 U | 9/2010 |
| CN | 103844359 A | 6/2014 |
| CN | 203748680 U | 8/2014 |
| CN | 203986126 U | 12/2014 |
| CN | 204217898 U | 3/2015 |
| CN | 204466908 U | 7/2015 |
| CN | 104886776 A | 9/2015 |
| CN | 105768225 A | 7/2016 |
| CN | 106037011 A | 10/2016 |
| CN | 106136332 A | 11/2016 |
| CN | 106858725 A | 6/2017 |
| CN | 106880085 A | 6/2017 |
| CN | 107048479 A | 8/2017 |
| CN | 108926037 A | 12/2018 |
| EA | 201290392 A1 | 10/2012 |
| EA | 201270596 A1 | 11/2012 |
| EP | 1867357 A1 | 12/2007 |
| EP | 2732713 A1 | 5/2014 |
| EP | 2989912 A1 | 3/2016 |
| EP | 3039976 A1 | 7/2016 |
| EP | 3135139 A1 | 3/2017 |
| GB | 2497536 A | 6/2013 |
| JP | 2013521074 A | 6/2013 |
| JP | 3211213 U | 6/2017 |
| KR | 20090077899 A | 7/2009 |
| KR | 101552254 B1 | 9/2015 |
| KR | 10-2016-0044712 A | 4/2016 |
| KR | 20170073664 A | 6/2017 |
| RU | 103281 U1 | 4/2011 |
| RU | 2014117968 A | 11/2015 |
| RU | 2604313 C2 | 12/2016 |
| RU | 2606072 C2 | 1/2017 |
| RU | 2616556 C2 | 4/2017 |
| RU | 2631623 C2 | 9/2017 |
| RU | 2692497 C1 | 6/2019 |
| WO | WO-2009043202 A1 | 4/2009 |
| WO | WO-2011050943 A1 | 5/2011 |
| WO | WO-2011063970 A1 | 6/2011 |
| WO | WO-2012106739 A1 | 8/2012 |
| WO | WO-2013000967 A1 | 1/2013 |
| WO | WO-2013050934 A1 | 4/2013 |
| WO | WO-2013118299 A1 | 8/2013 |
| WO | WO-2014004648 A1 | 1/2014 |
| WO | WO-2014116974 A1 | 7/2014 |
| WO | WO-2014201432 A1 | 12/2014 |
| WO | WO-2015179388 A1 | 11/2015 |
| WO | WO-2016054580 A1 | 4/2016 |
| WO | WO-2016062771 A1 | 4/2016 |
| WO | WO-2016076178 A1 | 5/2016 |
| WO | WO-2016090426 A1 | 6/2016 |
| WO | WO-2016107768 A1 | 7/2016 |
| WO | WO-2016121143 A1 | 8/2016 |
| WO | WO-2016135342 A2 | 9/2016 |
| WO | WO-2016178377 A1 | 11/2016 |
| WO | WO-2016184824 A1 | 11/2016 |
| WO | WO-2016207407 A1 | 12/2016 |
| WO | WO-2017001818 A1 | 1/2017 |
| WO | WO-2017064324 A1 | 4/2017 |
| WO | WO-2017093357 A1 | 6/2017 |
| WO | WO-2017122196 A1 | 7/2017 |
| WO | WO-2017139662 A1 | 8/2017 |
| WO | WO-2017141358 A1 | 8/2017 |
| WO | WO-2017149154 A1 | 9/2017 |
| WO | 2017/187545 A1 | 11/2017 |
| WO | WO-2017194763 A2 | 11/2017 |
| WO | WO-2017194766 A1 | 11/2017 |
| WO | WO-2017216516 A1 | 12/2017 |
| WO | WO-2018020599 A1 | 2/2018 |
| WO | WO-2018083037 A1 | 5/2018 |
| WO | WO-2018100366 A2 | 6/2018 |
| WO | WO-2018141466 A1 | 8/2018 |
| WO | WO-2018178900 A1 | 10/2018 |
| WO | WO-2018206697 A2 | 11/2018 |

(56) References Cited

FOREIGN PATENT DOCUMENTS

| WO | WO-2019081571 A1 | 5/2019 | |
|---|---|---|---|
| WO | WO-2019081897 A1 | 5/2019 | |
| WO | WO-2022248708 A1 * | 12/2022 | ............. A24F 40/42 |

OTHER PUBLICATIONS

Office Action received for Chinese Patent Application No. 2018800685113, mailed on Dec. 22, 2022, 14 pages (5 pages of English Translation and 9 pages of Official Copy).
Office Action received for Russian Patent Application No. 2021129125, mailed on Aug. 17, 2022, 12 pages (Official Copy Only). .
Communication for the EP application. 18803870.7 mailed on Apr. 28, 2020, 4 pages.
Decision of Refusal mailed Jan. 18, 2022 for Japanese Application No. 2020-526244, 8 pages.
Extended European Search Report for Application No. 19216390.5, mailed on Mar. 26, 2020, 8 pages.
International Preliminary Report on Patentability for Application No. PCT/EP2018/079136, mailed on Feb. 5, 2020, 8 pages.
International Preliminary Report on Patentability for Application No. PCT/EP2018/079137, mailed on Mar. 26, 2020, 6 pages.
International Preliminary Report on Patentability for Application No. PCT/EP2018/079139, mailed on May 7, 2020, 8 pages.
International Preliminary Report on Patentability for Application No. PCT/EP2018/082411, mailed on Jun. 4, 2020, 7 pages.
International Search Report and Written Opinion for Application No. PCT/EP2018/079137, mailed on Jan. 31, 2019, 7 pages.
International Search Report and Written Opinion for Application No. PCT/EP2018/079139, mailed on Mar. 14, 2019, 09 pages.
International Search Report for Application No. PCT/EP2018/079136, mailed on Feb. 12, 2019, 5 pages.
International Search Report for Application No. PCT/EP2018/082411, mailed on Mar. 22, 2019, 3 pages.
Korean Office Action mailed Feb. 6, 2020 for Korean Application No. 10-2019-7027109, 15 pages.
Notice of Acceptance mailed Jun. 2, 2021 for Australian Patent Application No. 2018355717, 3 pages.
Notice of Allowance for Korean Application No. 10-2019-7027109, dated Jan. 22, 2021, 5 pages.
Notice of Reasons for Refusal for Japanese Application No. 2020-523030, mailed on Dec. 21, 2021, 10 pages.
Notice of Reasons for Rejection for Japanese Application No. 2020-523030, mailed on Jul. 6, 2021, 11 pages.
Notice to File a Response mailed Feb. 24, 2022 for Korean Application No. 10-2020-7011674, 10 pages.
Office Action and Examination Search Report for Canadian Patent Application No. 3,079,623, mailed on Dec. 29, 2021, 6 pages.
Office Action and search report mailed Nov. 6, 2020 for Russian Application No. 2020114662, 13 pages.
Office Action for Canadian Application No. 3,079,626, mailed Jul. 5, 2021, 7 pages.
Office Action for Canadian Application No. 3083326 mailed on Jul. 5, 2021, 4 pages.
Office Action for Japanese Application No. 2019-231762, mailed on Dec. 15, 2020, 6 pages.
Office Action For Japanese Application No. 2020-526244, mailed on Jul. 13, 2021, 20 pages.
Office Action for Korean Application No. 10-2020-7011666, mailed on Dec. 20, 2021, 13 pages.
Office Action For Russian Application No. 2020114650, mailed on Nov. 20, 2020, 9 pages.
Office action for the JP application. 2019-560324 mailed on Jul. 28, 2020, 7 pages.
Office Action mailed Apr. 7, 2021 for Chilean Application No. 202001064, 13 pages. .
Office Action mailed Apr. 14, 2022 for Russian Application No. 2021129125, 8 pages.
Office Action mailed Aug. 23, 2021 for Chilean Application No. 202001064, 16 pages.
On Sep. 8, 2020, the applicant presented, in the European phase, a new specification amended, with only 16 clauses, with three independent claims—EP3614870, 6 pages.
Search Report for Japanese Application No. 2020-523030, mailed Jun. 30, 2021, 28 pages.
Search Report for Russian Application No. 2020114658 mailed on Nov. 12, 2020, 3 pages.
Search Report for Russian Application No. 2020116788 mailed on Dec. 21, 2020, 2 pages.
Smoke in Style, "Hybrid Electronic Pipe Kit," retrieved from https://www.smokeinstyle.com/hybrid-electronic-pipe-, on Mar. 3, 2021, 8 pages.
Wikipedia., "Academic Dictionary Definition of Cartridge," 2022, Retrieved from the Internet: https://dic.academic.ru/dic.nsf/ruwiki/195029, 6 pages.
Written Opinion for Application No. PCT/EP2018/079136, mailed on Feb. 12, 2019, 7 pages.
Written Opinion for Application No. PCT/EP2018/082411, mailed on Mar. 22, 2019, 5 pages.

* cited by examiner

AEROSOL PROVISION DEVICE FOR GENERATING A FLOW OF AEROSOL

PRIORITY CLAIM

The present application is a Continuation of U.S. application Ser. No. 16/758,977, filed Apr. 24, 2020, which, in turn, is a National Phase entry of PCT Application No. PCT/EP2018/079139, filed Oct. 24, 2018, which claims priority from GB Patent Application No. 1717498.8, filed Oct. 24, 2017, each of which is hereby fully incorporated herein by reference.

TECHNICAL FIELD

The present disclosure relates to an aerosol provision device for generating an inhalable medium.

BACKGROUND

Smoking articles such as cigarettes, cigars and the like burn tobacco during use to create tobacco smoke.

Attempts have been made to provide alternatives to these articles that burn tobacco by creating products that release compounds without burning.

Examples of such products are heating devices which release compounds by heating, but not burning, the material. The material may be for example tobacco or other non-tobacco products, which may or may not contain nicotine.

As another example, there are so-called e-cigarette devices. These devices typically contain a liquid which is heated to vaporize the liquid to produce an inhalable vapor or aerosol. The liquid may contain nicotine and/or flavorings and/or aerosol-generating substances, such as glycerol. The known e-cigarette devices typically do not contain or use tobacco.

As yet another example, there are so-called hybrid devices. These hybrid devices typically contain separately a liquid and a chamber for containing a material. In typical examples the material may be tobacco or other flavor material. The liquid is heated to vaporize the liquid to produce an inhalable vapor or aerosol which passes through the chamber containing the material so that a property, such as a flavor, is imparted to the vapor or aerosol.

Typically, in a hybrid device the material chamber and the liquid chamber are arranged with the material chamber located downstream of the liquid chamber. In such devices, it is typical for the liquid chamber and the material chamber to be arranged linearly, with the material chamber closer to the mouth of a user (at a proximal end, or mouth end, of the hybrid device). The material chamber and liquid chamber in such devices can be said to be in a 'stacked' arrangement. This arrangement typically results in a device which is elongate in shape.

In such a linear hybrid device, in use, aerosol from the liquid chamber passes in a substantially straight path through the material chamber to reach the mouth end of the device for inhalation by a user. In some instances, the material, such as tobacco, may leak from the material chamber into a user's mouth due to close proximity of the material chamber to the mouth end of the device.

In hybrid devices where either of both of the tobacco chamber and the liquid chamber are removeable and/or replaceable, a stacked arrangement may be an impediment since the tobacco chamber may need to be removed to access the liquid chamber, or vice-versa.

Some heating of the material, such as tobacco, in the material chamber is typically necessary to release the desired compounds from the material in order to have the desired effect on the aerosol. Such heating may be done by heat transfer from the aerosol itself or the tobacco may be heated directly by a heating means. It is desirable to provide an optimal amount of heating to the material while minimizing energy consumption. Where a heating means directly heats the material, close proximity between the material chamber and the heating means is desirable to minimize the energy consumption for providing the required heating. The geometry of stacked hybrid devices often makes effective and efficient heating of the material difficult to achieve.

SUMMARY

According to a first aspect of the present disclosure, there is provided an aerosol provision device comprising: a first section for containing an aerosolizable substance from which a flow of aerosol can be generated; and a second section for containing a material; wherein, in use, a flow of aerosol generated from aerosolizable substance in the first section flows through material in the second section before being inhaled by a user; and wherein the first section and the second section are located in a side-by-side arrangement in the device.

The first section and the second section may be located such that, in use, a side of the first section is substantially co-located with a side of the second section and said sides are substantially parallel to a longitudinal axis of the device.

The first section may comprise a heating arrangement for generating aerosol from the aerosolizable substance; in use, the heating arrangement is adjacent to the second section and is arranged to heat material in the second section.

The heating arrangement may comprise at least a first heating element and a second heating element.

The first heating element and second heating element may be arranged in a common plane and the first heating element and second heating element may be arranged such that they are at substantially the same distance from the second section.

The aerosolizable substance may be a liquid and the first section may comprise a liquid reservoir, and the heating arrangement may comprise a wick arrangement for transporting liquid from the liquid reservoir to the first heating element and to the second heating element.

The wick arrangement may comprise a first wick for transporting liquid from the liquid reservoir to the first heating element and a second wick for transporting liquid from the liquid reservoir to the second heating element.

The first heating element and the second heating element may be controllable independently of each other.

The heating arrangement may be configured such that one of the first heating element and the second heating element may be activated when the other of the first heating element and the second heating element is in-active.

The first section may be configured such that in use air enters the device into the first section in a direction that is substantially perpendicular to the longitudinal axis of the device, and aerosol exits the first section into the second section in a direction that is substantially perpendicular to the longitudinal axis of the device.

The second section may be configured such that in use aerosol flows from a distal end to a proximal end of the second section through the material in a direction which is substantially parallel to the longitudinal axis of the device.

The second section may comprise an opening in a first side wall, and a first barrier may be arranged at the opening, wherein the first barrier is porous to the flow of aerosol and prevents material from exiting the second section through the opening, and wherein the device is configured such that the first side wall is located adjacent to the first section in use such that aerosol generated from the first section can enter the second section through the opening.

The first barrier may be a mesh.

The second section may comprise an upper portion; a lower portion; and a second barrier; wherein the lower portion is for receiving the material, and the second barrier is porous to the flow of aerosol and is arranged to prevent material in the lower portion from exiting the lower portion into the upper portion.

The second barrier may be a mesh.

The upper portion may comprise a second opening towards a proximal end of the second section, and a third barrier that is porous to the flow of aerosol is arranged towards the second opening to prevent material from exiting the second opening.

The third barrier may be a mesh.

The first section and second section may be provided as separate cartridges.

The second section may further comprise a mouthpiece which is integral with the second section.

The second section and mouthpiece may define a slot for receiving the first section in use.

The aerosol provision device may further comprise a device body, wherein the first section and second section are configured to be independently releasably attachable to the device body.

The first section may comprise a first reservoir for receiving a first aerosolizable substance and a second reservoir for receiving a second aerosolizable substance.

According to a second aspect of the disclosure there is provided a first cartridge for an aerosol provision device according to the first aspect, the first cartridge comprising the first section for containing an aerosolizable substance and being releasably connectable to the aerosol provision device.

The first cartridge may be for containing an aerosolizable liquid.

The first cartridge according to the second aspect may comprise any of the features described above for the first section in the first aspect.

According to a third aspect there is provided a second cartridge for an aerosol provision device according to the first aspect, the second cartridge comprising the second section for containing the material and being releasably connectable to the aerosol provision device.

The second cartridge may be for containing tobacco material.

The second cartridge according to the second aspect may comprise any of the features described above for the second section in the first aspect.

DETAILED DESCRIPTION

Figure 1:
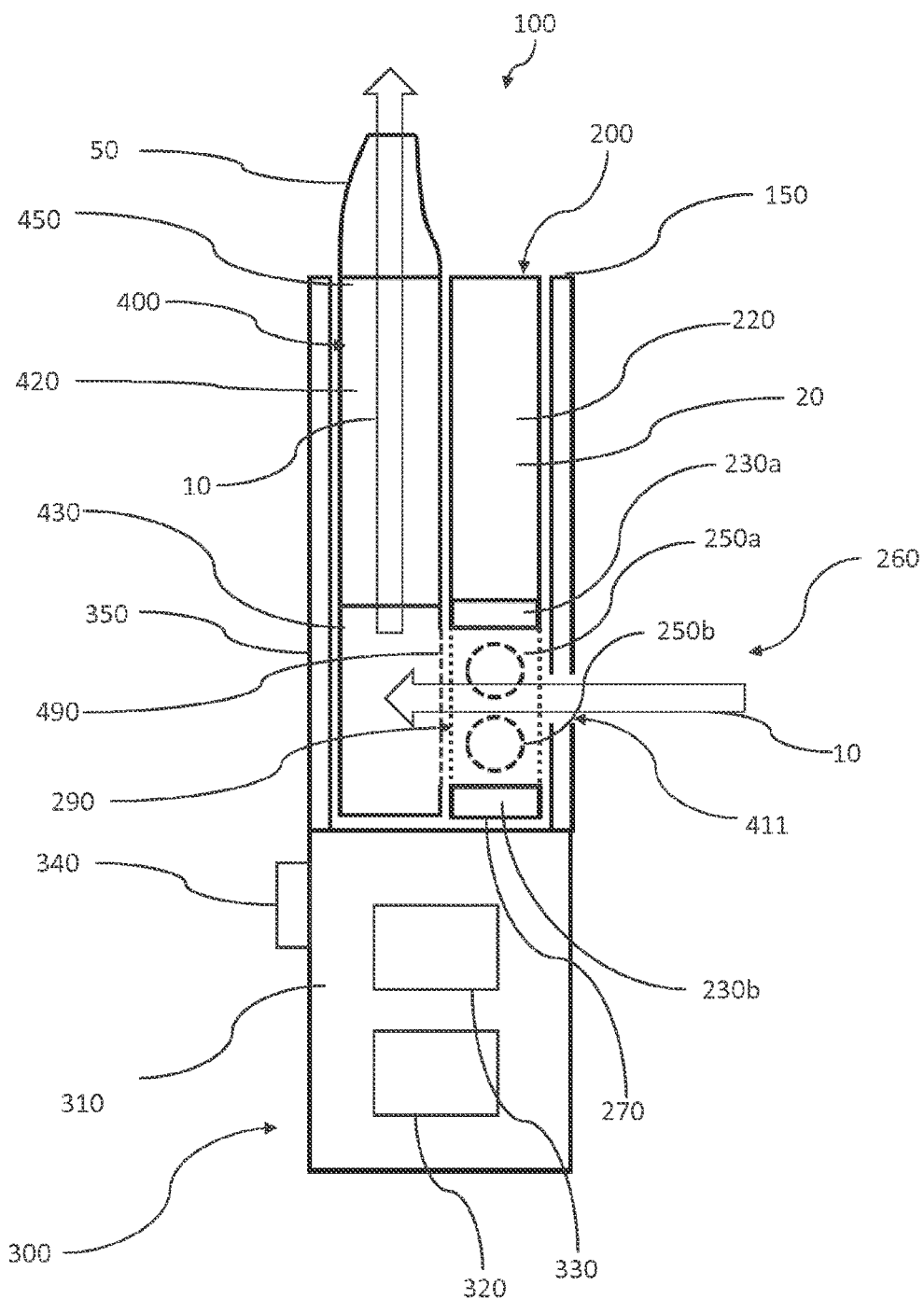
FIG. 1 is a schematic drawing of an example hybrid device according to the disclosure.

Referring to FIG. 1, a schematic of an aerosol provision device 100 is illustrated. The aerosol provision device 100 is an inhalation device (i.e. a user uses it to inhale an aerosol provided by the system 100) and the device 100 is a hand-held device. In this example, the device 100 is an electronic device.

In broad outline, the device 100 volatilizes an aerosol provision material 20 provided in an aerosol provision article 200. In this example the aerosol provision material 20 is a liquid, for example, an e-liquid, however in other examples the aerosol provision material may any other type of aerosolizable material, such as a gel. The device 100 in the example is a hybrid device since any aerosol and/or vapor produced from the aerosol provision article 200 passes through a material chamber 430 for containing a material (30, FIG. 2) before being inhaled by a user.

The material 30 may impart to or modify a property, for example the flavor, of the vapor and/or aerosol before the vapor and/or aerosol passes out of the device 100 for inhalation by a user. The material 30 may, for example, consist of or comprise tobacco. In the case that the material comprises tobacco, as the aerosol passes through and over the tobacco, the aerosol entrains organic and other compounds or constituents from the tobacco material that lend tobacco its organoleptic properties, thus imparting the flavor to the aerosol as it passes through the material chamber 430.

Suitable examples of the material 30 may comprise tobacco per se, different varieties of tobacco, tobacco derivatives, expanded tobacco, reconstituted tobacco, ground tobacco, tobacco extract, homogenized tobacco or tobacco substitutes. In the case of tobacco, the material 30, etc. may be in the form of a rod of tobacco, a pod or plug of tobacco, loose tobacco, agglomerates, etc., and may be in relatively dry form or in relatively moist form for example. The material 30 may be in the form of a plug of tobacco rod which is cut to length and placed into the material chamber 230. The material 30 may include other, non-tobacco, products, which, depending on the product, may or may not contain nicotine.

The material 30 may be for modifying a property of the aerosol other than (or in addition) to flavor.

In some examples, the material 30 may be or include a substance that modifies one or more other organoleptic properties of the aerosol (e.g. modifying the feel or smell or look of the aerosol to the user).

In some examples, the material 30 may be or include a substance that modifies the pH of the aerosol by either lowering or raising the pH (e.g. modifying the acidity or the basicity of the aerosol).

In some examples, the material 30 may be or include a substance that modifies (e.g. reduces) the amount of aldehydes in the aerosol.

In some examples, the material 30 may be or include a substance that modifies different combinations of two or more of these or indeed other properties of the aerosol flow.

It will be understood however that materials other than tobacco may be used to impart different flavors to the aerosol.

If the material 30 is or includes tobacco, it may be that the aerosol flow draws sufficient nicotine from the material 30. Alternatively or additionally, if the material 30 does not contain any tobacco, the material 30 may be enhanced with nicotine, for example by coating the material with nicotine. Indeed, even in the case that the material 30 is or includes tobacco, the material 30 may be coated or otherwise enhanced with nicotine. As another example, whether or not the material 30 is or includes tobacco and/or includes nicotine, nicotine may be provided in the aerosol provision material, in this example liquid 20. Accordingly, where it is intended that the system 100 provides nicotine for the user, the nicotine may be provided in the aerosol provision material, may be obtained from the material 30 in the case that the material is or includes tobacco, may be provided as a coating or the like on the material 30 if it is non-tobacco material, may be provided as a coating or the like on the material 30 if it is tobacco material, or any combination of these. Likewise, flavorings may be added to the material 30 (whether or not the substance is or includes tobacco) and/or to the aerosol provision material.

In at least some examples a vapor is produced that then at least partly condenses to form an aerosol before exiting the aerosol provision device through the material chamber for inhalation by a user (not shown).

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A "colloid" is a substance in which microscopically dispersed insoluble particles are suspended throughout another substance.

For reasons of convenience, as used herein the term aerosol should be taken as meaning an aerosol, a vapor or a combination of an aerosol and vapor.

Returning to FIG. 1, the hybrid device 100 comprises a first section 200, in this example an aerosol provision cartridge 200 (referred to in some instances below as a liquid cartridge), a device body 300, and a second section for receiving a material, in this example a material cartridge 400. In this example the material cartridge 400 comprises a mouthpiece 50 which may be formed integrally with the material cartridge or releasably detached at an upper end (or proximal or mouth end since it is the end closest to the mouth of a user in use) 450 of the material cartridge 400.

The device body 300 comprises a device body lower housing 310 which contains a power source 320, typically a battery, for powering various components of the device 100. The battery 320 may be a rechargeable battery or a disposable battery. A controller 330, which may comprise a microchip and associated circuitry is also provided in the lower housing 310 for controlling the operation of various components of the device 100. A user input means 340, for example one or more control buttons, may be provided on the exterior of the lower housing 310 for a user to operate the controller 330.

In this example, the device body 300 also comprises an upper housing 350 which extends to a proximal end 150 of the device 100 and defines a cavity into which the liquid cartridge 200 and the material cartridge 400 are inserted. In other examples, the device body 300 may comprise no upper housing and the liquid and material cartridges may attach only to a lower device housing, or the power source and control electronics may be comprised by the liquid cartridge or the material cartridge in which cases the device need comprise no device body.

As can be seen from FIG. 1, the liquid cartridge 200 and material cartridge 400 are located in a side-by-side arrangement. Herein 'side-by-side' means that a side of the liquid section is substantially co-located with a side of the material section and said sides are substantially parallel to a longitudinal axis of the device. This contrasts with typical hybrid devices in which the material and liquid cartridges are arranged linearly, end-to-end.

The side-by-side arrangement provided by the present invention differs from linear hybrid devices and provides for a more compact device. Furthermore, the present invention allows for either the liquid cartridge or the material cartridge to be independently detached from the device, which may not be possible in linear hybrid devices.

In this example, an upper, or proximal, portion of the liquid cartridge 200 comprises a liquid reservoir 220 containing liquid 20 and a lower, or distal, portion of the liquid cartridge 200 comprises an aerosolizing portion 260 for aerosolizing liquid 20 from the liquid reservoir 220. In this example, the aerosolizing portion 260 comprises a heating arrangement.

In some embodiments, the aerosolizing portion 260 may comprise at least one wick supplying liquid to at least one heating element to aerosolize liquid 20. The heating arrangement may comprise a plurality of heating elements wherein each heating element may be a straight heating element or a coil. Each wick may supply one heating element or may supply all or any number of the heating elements.

In the heating arrangement of this example, liquid 20 is supplied from the liquid reservoir 220 by a first wick 240a (FIG. 3) to be aerosolized by a first heating coil 250a and by a second wick 240b (FIG. 3) to a second heating coil 250b. More details of the operation of this two-coil system will be discussed below with reference to FIGS. 3 and 5.

In other examples the aerosolizing portion 260 may not comprise heating means or may not comprise a wick, and may comprise an ultrasonic atomizer, for example.

The liquid 20 can be a liquid that is volatilizable at reasonable temperatures, such as in the range of 100-300° C. or more particularly around 150-250° C., as that helps to keep down the power consumption of the system 100. Suitable materials include those conventionally used in e-cigarette devices, including for example propylene glycol and glycerol (also known as glycerine). Advantageously, the first and second heating coils 250a, 250b are positioned so as to also heat the material 30 in the chamber 430 and thereby enhance the effect the material 30 has on aerosol flowing through the material.

The liquid cartridge bottom end, or distal end 270 in this example comprises electrical contact points (not shown) for forming an electrical connection with the device body lower housing 310. As such, the first heating coil 250a, and second heating coil 250b are powered by the battery 320 and controlled by the controller 330.

Accordingly, in use, a user draws on the mouthpiece 50 and air is drawn through one or more air inlets 411 (the flow of this air is represented in FIG. 1 by block arrow 10). In this example, air is drawn into the device 100 through the one or more air inlets 411 in a direction that is substantially perpendicular to a longitudinal axis of the device 100. The heating coils 250a, 250b are powered by the user operating the control button 340 (or alternatively by a puff detector (not shown), as is known per se) and liquid 20 is drawn from the liquid reservoir 220 via first wick 240a and second wick 240b and is heated by the coils to volatize the liquid 20 and generate aerosol.

The aerosolizing portion 260, comprising the heating coils 250a, 250b, comprises an open section 290 (represented in FIG. 1 by dotted lines). This open section 290 is a window (shown in FIG. 3) which allows air drawn through the air inlet 411 to reach the coils 250a, 250b, where the air mixes with generated aerosol. The flow 10 then leaves the liquid cartridge 200 as a flow of aerosol-entrained air (hereinafter referred to simply as aerosol flow) to enter the material cartridge 400.

The material cartridge 400 comprises a material chamber 430 in which a material 30 is contained. The material cartridge 400 comprises a first housing having a porous section 490 (shown as a broken line in FIG. 1) in the inner wall of the first housing, i.e. the wall of the first housing which faces the liquid cartridge 200.

Figure 5:
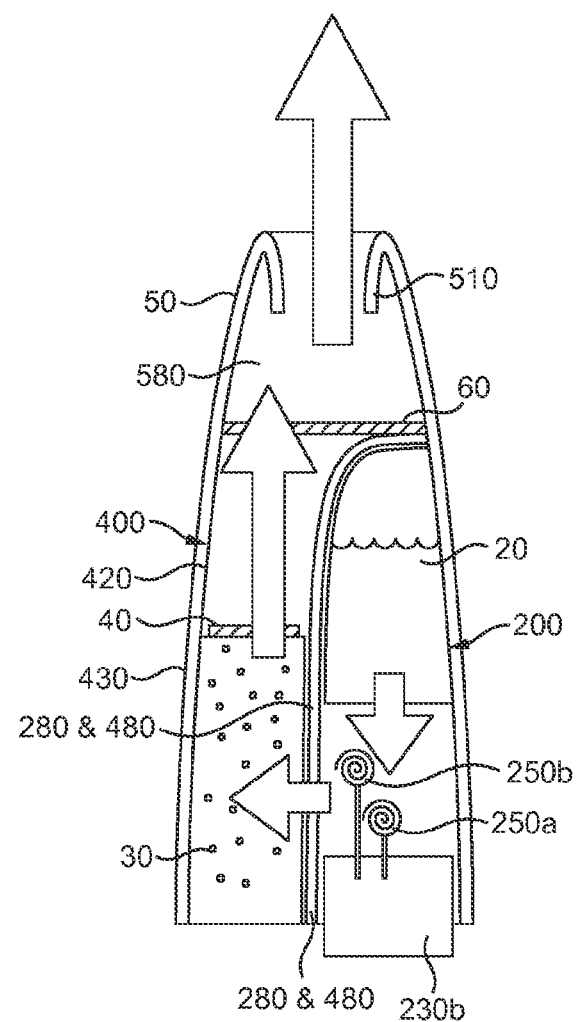
FIG. 5 is a schematic drawing of an example liquid cartridge, material cartridge and mouthpiece.

As discussed previously, in use the liquid cartridge 200 and material cartridge 400 are located side-by-side. The open section 290 of the liquid cartridge 200 is aligned with the porous section 490 of the material cartridge 400. A first seal 280 (FIG. 3) extends around the open section 290 while a second seal 480 (FIG. 2) extends around the porous section 490. The first seal 280 and second seal 480 abut against each other (as indicated in FIG. 5) and form a sealed passageway for aerosol passing from the liquid cartridge open section 290, through the material cartridge porous section 490, and into the material chamber 430.

As such, when a user draws on the device, aerosol flow 10 is drawn from the aerosolizing portion 260 into the material chamber 430 through the porous section 490. The aerosol flow 10 is drawn through the material chamber 430, in a direction that is parallel to the longitudinal axis of the device 100, towards the mouthpiece 50, passing through the material 30, in this example a tobacco material. As the aerosol flow 10 passes through the material 30, one or more components of the material 30 become entrained in the aerosol flow which may alter, or add to, a property of the aerosol, such as its taste.

It can be seen (from FIG. 1, and FIG. 5, for example) that since the liquid cartridge 200 and the material cartridge 400 are located side-by-side in use, the material chamber 430 is situated adjacent the lower portion of the liquid cartridge 260, which comprises the first heating coil 250a and second heating coil 250b. As such, the material 30, in this case tobacco material, is in close proximity with the first heating coil 250a and second heating coil 250b and the tobacco 30 can be heated directly by the heating coils 250a, 250b.

An additional advantage of this side-by-side arrangement is that the material chamber 430 presents a larger surface area facing the heating coils 250a, 250b. As such, more effective, uniform, heating of the tobacco can be achieved than in a typical linear hybrid device. The aerosol passing through the material is better enhanced as a result of this more effective heating.

Figure 3:
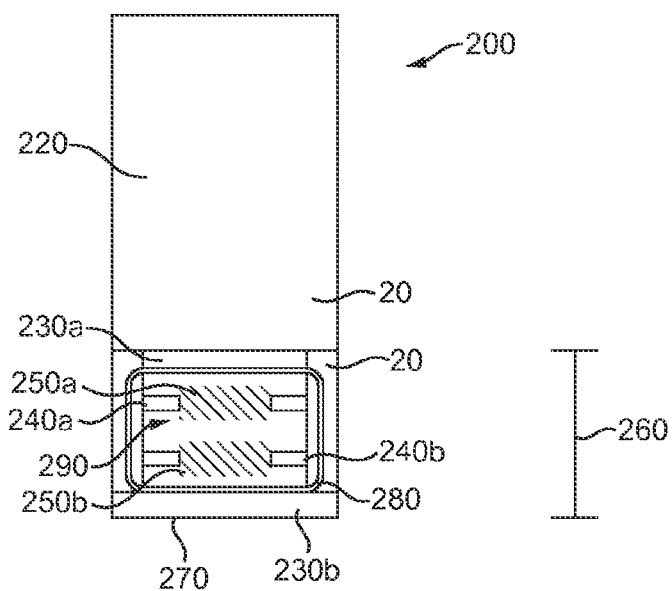
FIG. 3 is schematic side view drawing of an example liquid cartridge for use in the hybrid device of FIG. 1.

The side-by-side arrangement also allows for a relatively large porous section 490, which is in some examples substantially quadrilateral in shape as seen in FIG. 3. The porous section 490 presents a large surface area for aerosol transfer 10 from the liquid cartridge 200 to the material chamber 430. A further advantage of the side-by-side arrangement is that it provides for a shorter path for the aerosol flow 10. As such, less heat is lost by the aerosol flow and a warmer vapor can be delivered, both to the material and to the user. These features contribute to the material 30 more effectively altering the properties of the aerosol, since more, warmer, aerosol is delivered to a larger surface area of material 30 than in a linear device.

In use, and particularly in the case that the material is tobacco, the tobacco, or at least the surface of the tobacco, can be heated to a temperature of between around 190° C. to 210° C., such as around 200° C. so as to ensure that an adequate or appropriate amount of the compounds are released from the tobacco. The amount of tobacco present may be for example in the range 50 to 300 mg or so. A most suitable value for the amount of tobacco may be for example in the range 50 to 150 mg, with 130 mg being a value that is currently found to be particularly suitable in some applications. In a typical example, the amount of tobacco that is heated per operation of the system (i.e. per puff) may be in the corresponding range of around 8 to 50 mg.

Figure 2:
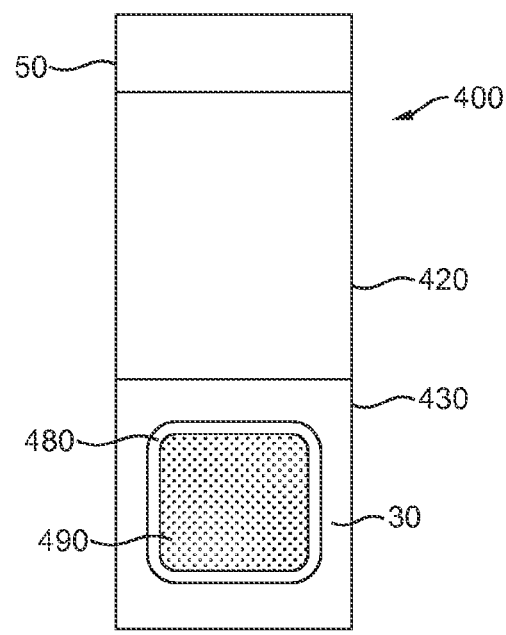
FIG. 2 is schematic side view drawing of an example material cartridge for use in the hybrid device of FIG. 1.

Turning now to FIG. 2 a schematic side view of the example material cartridge 400 of FIG. 1 is shown. The material 30, is contained in a lower portion 430 of the material cartridge 400. A porous membrane 490 is provided in the wall configured to face the liquid cartridge 200 in use. In this example the porous membrane 490 comprises a soft fine mesh but in other examples the porous membrane may be any porous barrier suitable for containing a material 30, such as solid tobacco material, in the material chamber 430 while being porous to the flow of aerosol into the chamber. The porous membrane 490 allows aerosol flow 10 from the liquid cartridge 200 to pass into the tobacco material 30 as discussed above with reference to FIG. 1. The porous membrane 490 may comprise a plastics material, such as polypropylene, or a metal, such as stainless steel or aluminum, and may comprise, for example, an aluminum foil. The porous membrane 490 may have a thickness of between about 0.1 mm and about 1.2 mm and, for example, may have a thickness of around 1.2 mm when the porous membrane 490 comprises a plastics material and, a thickness of around 0.1 mm when the porous membrane comprises a metal. The porous membrane 490 is advantageously a mesh with a maximum aperture size which is advantageously smaller than the diameter of the material 30 to be contained. For example, where the material 30 is tobacco, the maximum mesh aperture size may be between about 0.2 mm and about 0.7 mm, and the maximum mesh aperture size may be chosen dependent on the type of tobacco used.

As another advantage, the porous membrane contains the material 30 in place while allowing a user to have sensory interaction with the material 30 inside the material cartridge 400 before the cartridge is attached to the device 100. For example, if the material 30 is tobacco, a user can smell the tobacco through the porous membrane 490 while handling the tobacco cartridge 400. In this example, at least part of the material chamber 230 is transparent, allowing the user to see the tobacco and further enhancing the user's sensory experience. The second seal 480 extends around the porous section 490 to hold the porous membrane in place and prevent material 30 escaping the material cartridge 400. The porous membrane 490 is heat resistant to withstand heat generated from the heating coils 250a, 250b.

Figure 4A:
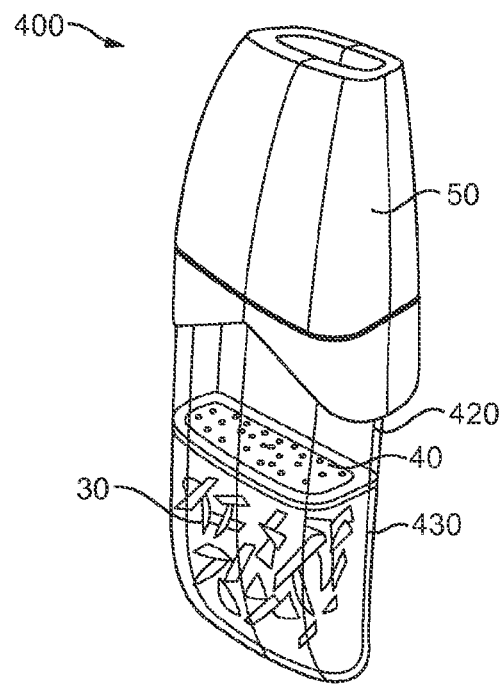
FIG. 4a is a perspective drawing of an example material cartridge and mouthpiece viewed from a first side.
Figure 4B:
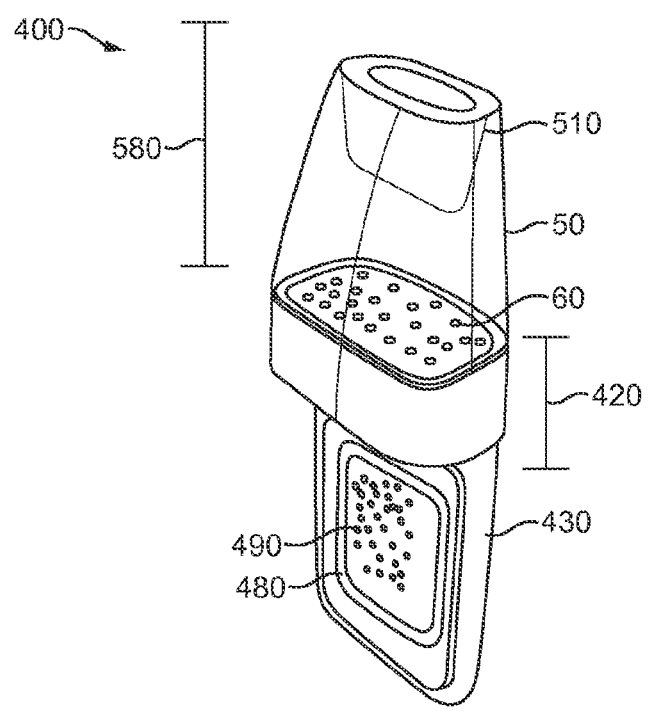
FIG. 4b is a perspective drawing of the example material cartridge and mouthpiece of FIG. 4a viewed from a second side.

FIG. 4a shows a first perspective view of the material cartridge 400, having a mouthpiece 50, viewed from a first, outer, side with a lower portion of the cartridge shown in a partial sectional view. FIG. 4b shows a second perspective view of the same material cartridge from a second, inner, side, with the mouthpiece 50 upper section of the cartridge shown in a partial sectional view.

FIG. 4a shows the outer side of the cartridge 400, that is, the side which would not be adjacent the liquid cartridge 200 in use. A first barrier 40 extends substantially horizontally across the top of the material chamber 430 of the tobacco cartridge 400, confining the tobacco 30 to the material chamber 430. The first barrier 40 is porous to the flow of aerosol (10, FIG. 1) but prevents the exiting of material 30 from the material chamber 430 into the material cartridge upper portion 420. In this example, the first barrier 40 is a mesh. In examples where the first barrier 40 is a mesh the mesh may comprise any of the materials discussed above for the porous membrane 490. The first barrier 40 is advantageously a heat resistant material capable of withstanding temperatures up to about 180° C.

In this example, the mouthpiece 50 is attached to the tobacco cartridge 400. In other examples, the mouthpiece 50 may be detachably attached to the tobacco cartridge. In yet other examples, the mouthpiece 50 may be formed integrally with the material cartridge 400. At the top of the upper portion 420 of the tobacco cartridge 400 a second barrier 60 extends substantially horizontally. The second barrier 60 provides additional protection against material 30 from the material chamber 430 being inadvertently inhaled by a user. Furthermore, the second mesh is provided at a vertical distance from a mouth aperture 510 of the mouthpiece 50. This vertical distance provides a mouthpiece chamber 580 which contributes to reducing leakage from the material 30 passing into the user's mouth. When aerosol passes through a material 30, such as tobacco, some of the aerosol may condense to a condensate. In example devices where the material is too close to the mouth of a user, the condensate may escape the device into the user's mouth. The vertical distance between material 30 and the mouthpiece 50 provided by the second barrier 60 contributes to preventing any condensate reaching the user's mouth. The tobacco cartridge 400 of this example can also be seen in FIG. 5 where the upper portion 420 of the tobacco chamber and mouthpiece chamber may be seen in a schematic cross-sectional view.

It can be seen from FIG. 4b and FIG. 5 that the material chamber 430 has a width which is smaller than the width of the top of the material cartridge upper section 420. In this example, the mouthpiece 50 is attached to the top of the material cartridge 400 which expands in width towards its proximal end. The material cartridge 400 has an inner side which is substantially parallel to a longitudinal axis of the device 100 at the material chamber 430 but which curves such that the width of the material cartridge 400 increases towards the top of the material cartridge upper section 420. The inner side of the material cartridge 400 is thereby shaped to accommodate the liquid cartridge 200, as shown in FIG. 5, when the two are placed side-by-side.

FIG. 3 shows a schematic side view of the liquid cartridge 200 of FIG. 1. The liquid cartridge comprises a liquid reservoir 220 containing a liquid 20. A distal portion of the liquid cartridge 200 comprises an aerosolizing portion 260. The aerosolizing portion 260 comprises a comprises a first wick 240a for supplying liquid 20 from the liquid reservoir 220 to a first heating coil 250a and a second wick 240b for supplying liquid 20 to a second heating coil 250b. The liquid reservoir 220 in this example extends down both sides of the aerosolizing portion 260 of the cartridge 200 and the first and second wicks 240a, 240b draw from both sides of the lower portion of the liquid reservoir 220.

The first and second wicks 240a, 240b are in fluidic contact with the liquid 20 contained in the liquid reservoir 220. The wicks 240a, 240b are generally absorbent and act to draw in liquid 20 from the liquid reservoir 220 by capillary action. The wicks 240a, 240b can be non-woven and may be for example a cotton or wool material or the like, or a synthetic material, including for example polyester, nylon, viscose, polypropylene or the like, or a ceramic material.

As mentioned above with reference to FIG. 1, the aerosolizing portion 260 comprises an open section 290 which allows air to flow in from the air inlets 411 to entrain aerosol produced at the first coil 250a and second coil 250b. A second seal 280 extends around the open section 290. The aerosolizing portion 260 comprises an upper bar 230a which is a solid bar extending across the width of the open section 290 at the proximal end of the aerosolizing portion 260. A lower bar 230b is also included which is a solid bar extending across the width of liquid cartridge 200 at the cartridge's distal end 260. The lower bar 230b comprises electrical contacts 270 for connecting the heating coils 250a, 250b to the device body 300.

Heating the material 30 is an important factor in providing the user with a satisfactory sensory experience. For example, if the material 30 comprises tobacco, then heating the tobacco increases the tobacco taste amplitude experienced by a user and may cause more constituents such as nicotine to become entrained in the flow of aerosol.

Using a heating arrangement that comprises at least a first heating element and second heating element that are arranged to heat the material 30 provides for an efficient heat transfer to the material 30 and enables a relatively large surface area of the substance 30 to be heated. Additionally, the power consumed per heating element may be less than would need to be consumed by an element in a heating arrangement in which that element was the only element.

The first heating element 250a and the second heating element 250b are located adjacent to the chamber 430 when the liquid cartridge 200 and material cartridge 400 are side-by-side. Accordingly, the first heating element 250a and the second heating element 250b are located close enough to the chamber 430 so as to be able to heat and raise the temperature of the substance 30 when the first heating element 250a and the second heating element 250b are activated.

The first heating element 250a and second heating element 250b in this example are arranged in a common plane which is substantially parallel to the porous section 490 of the material chamber 430. This arrangement facilitates a uniform heating of the substance 30 in the chamber 430.

The first heating element 250a and the second heating element 250b may be elongate and arranged substantially in parallel, again to ensure a uniform heating of the substance 30 in the chamber 230.

Each of the first heating element 250a and the second heating element 250b may be an electrically resistive heater, including for example a nichrome resistive heater, a ceramic heater, etc. In the illustrated example, the first heating element 250a and the second heating element 250b is a wire, which is in the form of a coil. Each of the first heating element and the second heating element may be a linear coil, a curved coil, a bottom vertical coil, or a spiral coil.

In alternative examples, each of the first heating element 250a and the second heating element 250b may be in the form of a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc.

Other heating arrangements may be also used for the first heating element 250a and the second heating element 250b, including non-electrical heating arrangements, or other electrical heating arrangements, for example, each of the first heating element 250a and the second heating element 250b may be an induction heating element.

In the example shown in the figures, the first heating element 250a and the second heating element 250b are substantially linear (i.e. straight) resistive heating coils and each surrounds a respective wick 240a, 240b which is in (thermal) contact with its heating element 250a or 250b. The wicks 240a, 240b are also in fluidic contact with the liquid 20 contained in the liquid reservoir 220. The wicks 240a, 240b are generally absorbent and act to draw in liquid 20 from the liquid reservoir 220 by capillary action.

The wicks 240a, 240b can be non-woven and may be for example a cotton or wool material or the like, or a synthetic material, including for example polyester, nylon, viscose, polypropylene or the like, or a ceramic material.

In some examples, the control circuitry 330 is configured to able to independently control the activation of the first heating element 250a and the second heating element 250b.

In these examples, the control circuitry 330 may be configured to be able to activate one of the first heating element 250a and the second heating element 250b while the other of the first heating element 250a and the second heating element 250b is inactive.

In use, and particularly in the case that the material 30 is tobacco, the tobacco, or at least the surface of the tobacco, can be heated to a temperature of between around 190° C. to 210° C., for example around 200° C. so as to ensure that an adequate or appropriate amount of the compounds are released from the tobacco.

The amount of tobacco present may be for example in the range 50 to 300 mg or so. A most suitable value for the amount of tobacco may be for example in the range 50 to 150 mg, with 130 mg being a value that is currently found to be particularly suitable in some applications. In a typical example, the amount of tobacco that is heated per operation of the system (i.e. per puff) may be in the corresponding range of around 8 to 50 mg.

Figure 6:
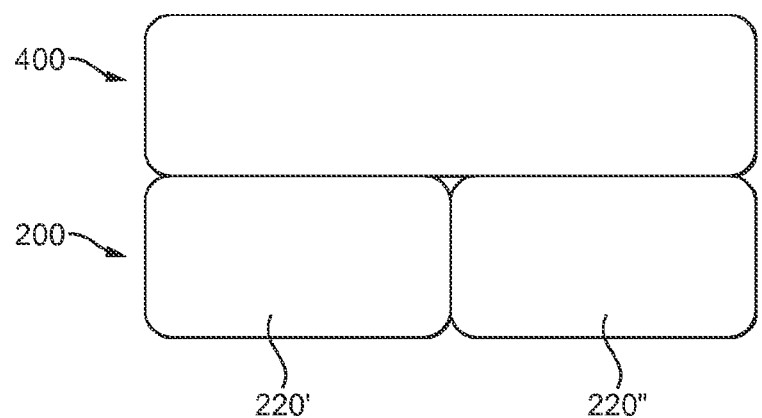
FIG. 6 is a schematic drawing of a material cartridge, and a liquid cartridge having two liquid reservoirs, viewed from above.

The side-by-side arrangement of the aerosol provision cartridge 200 and material cartridge 400 allows for the aerosol provision cartridge 200 to comprise two reservoirs for aerosolizable substances, for example containing liquids of different flavors. In the example shown in FIG. 6, the cartridge 200 comprises a first liquid reservoir 220' and a second liquid reservoir 220", and the liquid cartridge 200 is split vertically such that the first liquid reservoir 220' occupies a first section of the cartridge while the second liquid reservoir 220" occupies a second section of the cartridge.

In some embodiments, the device 100 may further comprise a hygienic cap (not shown) for covering at least a portion of the device 100, for example the mouthpiece 50, and for keeping the portion of the device 100 clear when placed, for example, in the bag or pocket of a user. The hygienic cap may also provide aesthetic benefits and may comprise, for example, a metal finish, patterns on its surface, or alternative colors, etc. The device 100 may be inserted into the hygienic cap either with the proximal end of the device first, or the distal end of the device first. The hygienic cap may also, in some examples, comprise contacts inside which may contact user input means 340 and allow a user to initiate the device 100 while the cap is still on the device.

As used herein, the terms "flavor" and "flavorant" refer to materials which, where local regulations permit, may be used to create a desired taste or aroma in a product for adult consumers. They may include extracts (e.g., licorice, *hydrangea*, Japanese white bark *magnolia* leaf, chamomile, fenugreek, clove, menthol, Japanese mint, aniseed, cinnamon, herb, wintergreen, cherry, berry, peach, apple, Drambuie™, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, *cassia*, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder.

In order to address various issues and advance the art, the entirety of this disclosure shows by way of illustration and example various embodiments in which the claimed invention may be practiced and which provide for a superior system arranged to generate an inhalable medium. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. An aerosol provision device comprising:
a first section for containing an aerosolizable substance from which a flow of aerosol can be generated; and
a second section for containing a material;
wherein, in use, a flow of aerosol generated from aerosolizable substance in the first section flows through material in the second section before being inhaled by a user; and wherein the first section and the second section are located in a side-by-side arrangement in the aerosol provision device and wherein the first section is a cartridge which is releasably connectable to the aerosol provision device, and wherein the first section is configured such that in use air enters the aerosol provision device into the first section in a direction that is substantially perpendicular to a longitudinal axis of the aerosol provision device.

2. The aerosol provision device according to claim 1, wherein the first section and the second section are located such that a side of the first section is substantially co-located with a side of the second section, and the side of the first section and the side of the second section are substantially parallel to the longitudinal axis of the device.

3. The aerosol provision device according to claim 1, wherein the first section comprises a heating arrangement for generating aerosol from the aerosolizable substance; and
in use, the heating arrangement is adjacent to the second section and is arranged to heat the material in the second section.

4. The aerosol provision device according to claim 3, wherein the heating arrangement comprises at least a first heating element and a second heating element.

5. The aerosol provision device according to claim 4, wherein the first heating element and the second heating element are at least one of:
- arranged in a common plane and at substantially the same distance from the second section;
- resistive heating coils;
- substantially linear resistive heating coils;
- bottom vertical coils or spiral coils;
- controllable independently of each other; or
- one of the first heating element or the second heating element may be activated when the other of the first heating element or the second heating element is inactive.

6. The aerosol provision device according to claim 1, wherein the aerosolizable substance is a liquid and the first section comprises a liquid reservoir, and the heating arrangement comprises a wick arrangement for transporting the liquid from the liquid reservoir to the first heating element and to the second heating element, wherein the wick arrangement comprises a first wick for transporting the liquid from the liquid reservoir to the first heating element and a second wick for transporting the liquid from the liquid reservoir to the second heating element.

7. The aerosol provision device according to claim 1, wherein at least one of:
- the first section is configured such that aerosol exits the first section into the second section in a direction that is substantially perpendicular to the longitudinal axis of the aerosol provision device, or
- the second section is configured such that in use aerosol flows from a distal end to a proximal end of the second section through the material in a direction which is substantially parallel to the longitudinal axis of the aerosol provision device.

8. The aerosol provision device according to claim 1, wherein the second section comprises an opening in a first side wall, and a first barrier is arranged at the opening, and the first barrier is porous to the flow of the aerosol and prevents the material from exiting the second section through the opening, wherein the aerosol provision device is configured such that the first side wall is located adjacent to the first section in use such that the aerosol generated from the first section can enter the second section through the opening, and wherein at least one of:
- the second section comprises:
  - an upper portion,
  - a lower portion, and
  - a second barrier, wherein
    - the lower portion is for receiving the material, and the second barrier is porous to the flow of the aerosol and is arranged to prevent the material in the lower portion from exiting the lower portion into the upper portion;
    - the upper portion comprises a second opening towards a proximal end of the second section, and a third barrier that is porous to the flow of the aerosol is arranged towards the second opening to prevent the material from exiting the second opening; or
- at least one of the first barrier, the second barrier, or the third barrier is a mesh.

9. The aerosol provision device according to claim 1, wherein the first section and the second section are provided as separate cartridges.

10. The aerosol provision device according to claim 1, further comprising a mouthpiece which is integral with the second section.

11. The aerosol provision device according to claim 10, further comprising a mouthpiece which is integral with the second section, wherein the second section and the mouthpiece define a slot for receiving the first section in use.

12. The aerosol provision device according to claim 9, further comprising a device body, wherein the first section and the second section are configured to be independently releasably attachable to the device body.

13. The aerosol provision device according to claim 1, wherein first section is a liquid cartridge and the second section is a tobacco cartridge for receiving a material comprising tobacco.

14. The aerosol provision device according to claim 1, wherein the first section comprises a first reservoir for receiving a first aerosolizable substance and a second reservoir for receiving a second aerosolizable substance.

15. A first cartridge for the aerosol provision device according to claim 1, the first cartridge comprising the first section for containing the aerosolizable substance and being releasably connectable to the aerosol provision device, wherein the first cartridge is configured such that in use air enters the aerosol provision device into the first cartridge in a direction that is substantially parallel to the longitudinal axis of the aerosol provision device.

16. The first cartridge according to claim 15, wherein the first cartridge comprises a reservoir for containing an aerosolizable substance and a heating arrangement for generating aerosol from the aerosolizable substance; wherein, when in use in the aerosol provision device, the heating arrangement is adjacent to the second section and is arranged to heat the material in the second section.

17. The first cartridge according to claim 16, wherein the heating arrangement comprises at least a first heating element and a second heating element.

18. The first cartridge according to claim 17, wherein at least one of:
- the first heating element and the second heating element are arranged in a common plane and the first heating element and the second heating element are arranged at substantially the same distance from the second section;
- the first heating element and the second heating element are resistive heating coils;
- the first heating element and the second heating element are substantially linear resistive heating coils;
- the first heating element and the second heating element are bottom vertical coils or spiral coils;
- the first heating element and the second heating element are bottom vertical coils or spiral coils;
- the first heating element and the second heating element are controllable independently of each other; or
- one of the first heating element or the second heating element may be activated when the other of the first heating element or the second heating element is inactive.

19. The first cartridge according to claim 15, wherein the aerosolizable substance is a liquid and the first cartridge comprises a liquid reservoir, and the heating arrangement comprises a wick arrangement for transporting the liquid from the liquid reservoir to the first heating element and to the second heating element.

20. The first cartridge according to claim 19, wherein the wick arrangement comprises a first wick for transporting the liquid from the liquid reservoir to the first heating element and a second wick for transporting the liquid from the liquid reservoir to the second heating element.

21. The first cartridge according to claim 15, wherein the first cartridge is configured such that aerosol exits the first section into the second section in a direction that is substantially perpendicular to the longitudinal axis of the aerosol provision device.

22. A cartridge for the aerosol provision device according to claim 1, the cartridge comprising the second section for containing the material and being releasably connectable to the aerosol provision device.

23. The cartridge according to claim 22, wherein the cartridge is configured such that in use aerosol flows from a distal end to a proximal end of the cartridge through the material in a direction which is substantially parallel to the longitudinal axis of the aerosol provision device.

24. The cartridge according to claim 22, wherein the cartridge comprises an opening in a first side wall, and a first barrier is arranged at the opening, and the first barrier is porous to the flow of aerosol and prevents the material from exiting the cartridge through the opening, wherein the aerosol provision device is configured such that the first side wall is located adjacent to the first section in use such that aerosol generated from the first section can enter the cartridge through the opening.

25. The cartridge according to claim 24, the cartridge optionally comprising at least one of:

an upper portion,
a lower portion, and
a second barrier,
wherein the lower portion is for receiving the material, and the second barrier is porous to the flow of aerosol and is arranged to prevent the material in the lower portion from exiting the lower portion into the upper portion;
wherein the upper portion comprises a second opening towards a proximal end of the second section, and a third barrier that is porous to the flow of aerosol is arranged towards the second opening to prevent the material from exiting the second opening;
at least one of the first barrier, the second barrier, or the third barrier is a mesh.

26. The cartridge according to claim 22, further comprising a mouthpiece which is integral with the cartridge.

27. The cartridge according to claim 26, wherein the second section and the mouthpiece define a slot for receiving another cartridge in use, the another cartridge comprising the first section for containing the aerosolizable substance and being releasably connectable to the aerosol provision device.

28. The cartridge according to claim 22, wherein the cartridge is for containing a tobacco material.

* * * * *